(12) United States Patent
Schawe et al.

(10) Patent No.: US 6,170,984 B1
(45) Date of Patent: *Jan. 9, 2001

(54) APPARATUS AND METHOD FOR DIFFERENTIAL ANALYSIS USING REAL AND IMAGINARY SIGNAL COMPONENTS

(75) Inventors: Jürgen Schawe, Blaustein (DE); Marcel Margulies, Scarsdale, NY (US)

(73) Assignee: PerkinElmer Instruments LLC, Norwalk, CT (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/065,762

(22) Filed: Apr. 23, 1998

Related U.S. Application Data (63) Continuation of application No. 08/691,716, filed on Aug. 2, 1996, now abandoned, which is a continuation of application No. 08/252,597, filed on Jun. 1, 1994, now Pat. No. 5,549,387.

(51) Int. Cl.[7] .................................................. G01N 25/00
(52) U.S. Cl. ................................................. 374/10; 374/1
(58) Field of Search ................................ 374/10, 11, 12, 374/31, 1

(56) References Cited

U.S. PATENT DOCUMENTS

| | | | |
|---|---|---|---|
| 4,255,961 | * 3/1981 | Biltonen et al. . | |
| 4,517,021 | * 5/1985 | Schollmeier | 127/30 |
| 4,623,263 | * 11/1986 | Barberi et al. | 374/12 |
| 5,224,775 | * 7/1993 | Reading et al. . | |
| 5,599,104 | * 2/1997 | Nakamura et al. | 374/12 |
| 5,842,788 | * 12/1998 | Danley et al. | 374/10 |
| 5,988,875 | * 11/1999 | Gershfeld et al. | 374/10 |

FOREIGN PATENT DOCUMENTS

| | | |
|---|---|---|
| 35 29 489 | * 2/1987 | (DE) . |
| 0 645 619 | * 3/1995 | (EP) . |
| 1 431 111 | * 4/1976 | (GB) . |
| 2 075 675 | * 11/1981 | (GB) . |

OTHER PUBLICATIONS

"Complex plane analysis of heat capacity of polymers in the glass transition region.", *J. of Physics E: Scientific Instruments*, vol. 4, 1971, pp. 21–23, Aug. 1970.

Jorrnal of Thermal Analysis, An International Forum For Thermal Studies, 1994.*

* cited by examiner

*Primary Examiner*—Andrew H. Hirshfeld
(74) *Attorney, Agent, or Firm*—St. Onge Steward Johnston & Reens LLC (57) ABSTRACT

The invention is directed to a differential analysis method and apparatus wherein a sample and reference are subjected to an externally applied disturbance, such as temperature change, in accord with a prescribed function comprising the sum of a linearly changing part and a periodically changing part, and the measured differential signal is processed into real and imaginary components relating, respectively, to the energy storage and energy loss portions of the signal.

8 Claims, 7 Drawing Sheets

APPARATUS AND METHOD FOR DIFFERENTIAL ANALYSIS USING REAL AND IMAGINARY SIGNAL COMPONENTS

CROSS REFERENCE TO RELATED APPLICATIONS

This application is a continuation of application Ser. No. 08/691,716 filed Aug. 2, 1996, now abandoned, which is a continuation of application Ser. No. 08/252,597 filed on Jun. 1, 1994, now U.S. Pat. No. 5,549,387.

BACKGROUND OF THE INVENTION

The present invention relates to a method and apparatus for differential thermal analysis. Differential thermal techniques generally consist of applying heat simultaneously to a sample material and a reference material and measuring a parameter, such as differential power input, as the sample goes through a physical or chemical change. In differential thermal analysis (DTA), the sample and reference are heated or cooled according to a programmed rate, and the temperature differential between the sample and reference is measured as the scan proceeds. In differential scanning calorimetry (DSC), differential power rather than differential temperature is measured. The differential power represents the difference in energy required to maintain the sample and reference in accord with a heating or cooling program.

In addition to DSC and DTA, other differential thermal techniques also exist to measure basic properties that change with temperature. In differential dielectric analysis (DDA) a property of the sample (dielectric constant) is measured while the temperature is changed. Further, in differential thermogravimetric analysis (DTGA), differential weight loss of a sample is monitored as the temperature is increased.

In 1968, Sullivan and Seidel reported a non-differential thermal technique which is now known as AC calorimetry. P. F. Sullivan, G. Seidel, "Steady-State, AC-Temperature Calorimetry," Phys. Rev. 173(3), 679–685 (1968). This technique was later modified by Dixon et al. who, in 1982, reported a method called differential AC calorimetry. G. S. Dixon et al., "A Differential AC Calorimeter for Biophysical Studies," Anal. Biochem. 121(1), 55–61 (1982). Differential AC calorimetry, as described by Dixon et al., consists of heating or cooling the sample and reference at a linear rate with a sinusoidal oscillation superimposed on the linear heating or cooling program. Dixon et al. determined the heat capacity of the sample using the differential AC temperature response measured between the sample and reference.

U.S. Pat. No. 5,224,775, assigned to TA Instruments, Inc. (hereinafter "the '775 patent"), discloses the use of differential AC calorimetry in a method which deconvolutes the resulting differential signal as described by Dixon et al. The '775 patent discloses processing of the signal into "rapidly reversing" and "non-rapidly reversing" components. The thermodynamic significance of the "rapidly reversing" and "non-rapidly reversing" components is not apparent for time-dependent processes. For time-dependent thermal events (equilibrium processes), only the "rapidly reversing" component may have thermodynamic significance. Since most thermal events of interest, such as the glass transition of a polymeric material, are time-dependent processes, there is an obvious need for a more comprehensive method of processing the differential signal.

The present invention provides a method and apparatus for processing the differential signal into real (inphase) and imaginary (quadrature) components which are related to the "energy storage" and "energy loss" portions of the thermal event being studied. The inphase and quadrature components provide physical and thermodynamic information for thermal events which are time-independent or time-dependent.

SUMMARY OF THE INVENTION

The invention is directed to a differential analysis apparatus comprising (i) a sample holder and a reference holder, (ii) a thermal device for subjecting the sample and reference to an externally applied disturbance, such as temperature change, in accord with a prescribed function comprising the sum of a linearly changing part and a periodically changing part (iii) at least one computing device for receiving data representative of differential signals resulting from the sample and reference being subjected to the applied disturbance in accord with the prescribed function, and (iv) a device to process said data to provide at least one parameter, such as heat capacity, representative of said sample and to separate said at least one parameter into components relating to the energy storage (real) and energy loss (imaginary) portions of said at least one parameter.

The invention further comprises a method of analyzing a sample using a differential analysis apparatus comprising (i) subjecting a sample and reference to an externally applied disturbance, such as temperature change, in accord with a prescribed function comprising the sum of a linearly changing part and a periodically changing part, (ii) detecting a differential signal representative of at least one characteristic parameter of the sample, and (iii) processing said signal into components relating to the energy storage and energy loss portions of said at least one characteristic parameter.

DETAILED DESCRIPTION OF THE INVENTION

The present invention finds application in differential analysis methods and apparatus including, but not limited to, DTA, DSC, DDA, and differential photocalorimetry (DPC). While the following detailed description is provided with reference to DSC and DTA, the present invention is not limited to an apparatus comprising, or method employing, DSC and DTA. Further, a sinusoidal periodic function is adopted for the following description. However, the invention is not so limited, and any periodic function can be substituted for the sinusoidal function. The term "prescribed function" as used herein means any function which comprises the sum of a linearly changing part and a periodically changing part. The periodically changing part includes, but is not limited to, a sinusoidal function, a saw tooth function, a square wave function, or a pulse wave. While all periodic functions can be characterized by a period or frequency, certain periodic functions, such as sinusoidal functions, are also characterized, in addition, by an amplitude.

The linearly changing part can have a positive (heating), negative (cooling), or zero slope. In the case where the slope is zero, the prescribed function includes "isothermal functions" in which the sample and reference are subjected to a periodic temperature variation such that during the scan the average temperature of the sample and reference remains essentially constant.

Figure 1:
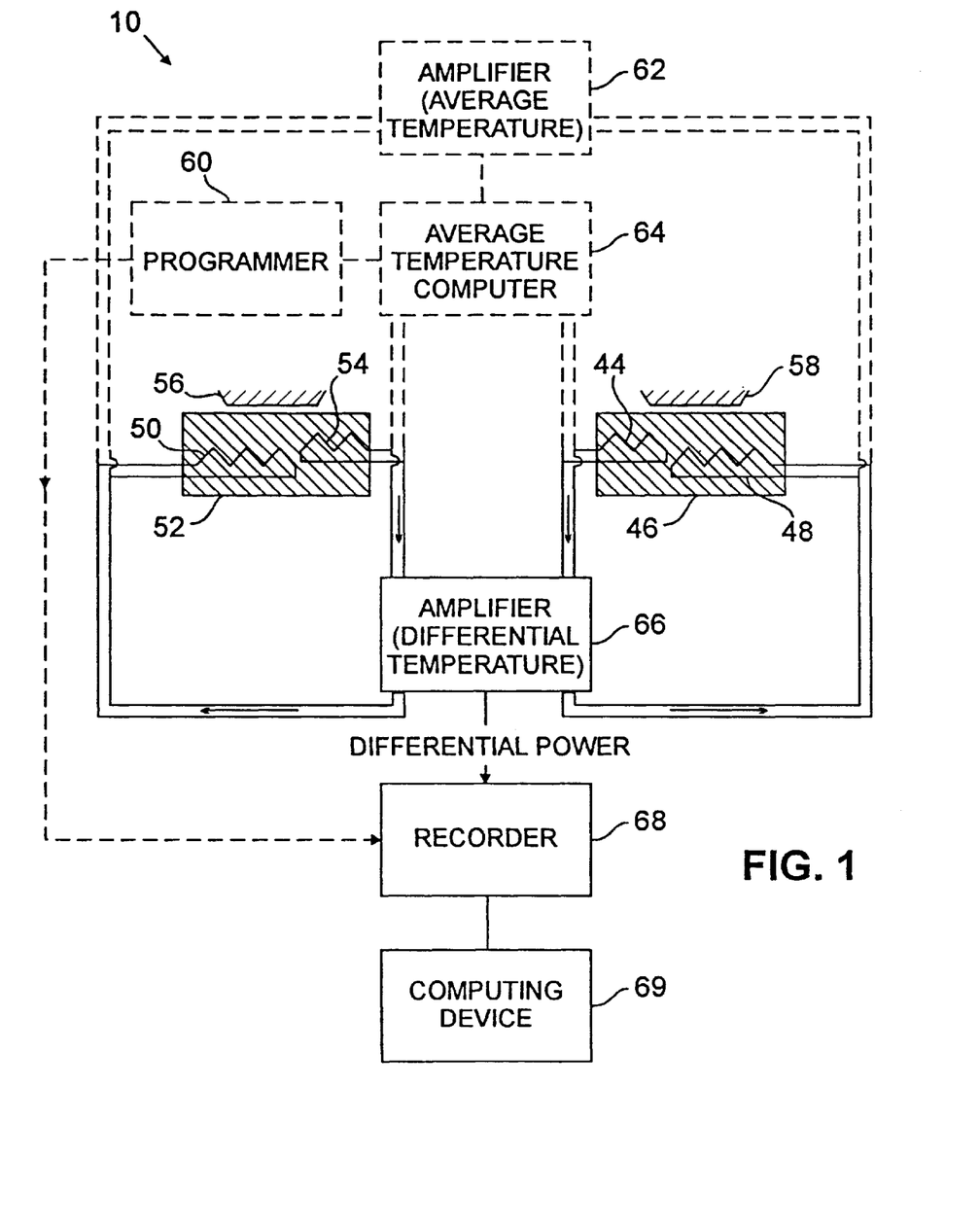
FIG. 1 is a schematic diagram illustrating a "power compensation" differential scanning calorimeter, which includes two control loops and is adapted to implement the present invention.

FIG. 1 illustrates a portion 10 of a DSC, for example, a Perkin-Elmer Corporation DSC-7 type of calorimeter, which can be used to implement the present invention. The user's manual to the DSC-7 calorimeter, entitled "Users Manual, 7 Series/Unix DSC7, Differential Scanning Calorimeter," is herein incorporated by reference. This instrument measures the differential power required to keep both sample and reference sensors 44, 54 at the same temperature throughout the DSC experiment. The apparatus, as illustrated, is described and explained in basic terms in E. S. Watson et al., "A Differential Scanning Calorimeter for Quantitative Differential Analysis," Anal. Chem. 36(7), 1233–1238 (1964), which is herein incorporated by reference.

In FIG. 1, reference and sample containers 56 and 58, respectively, are mounted on platforms 52 and 46. The reference generally is a standard (or simply the empty container) and the sample is a material having some characteristic parameter to be compared with that of the standard. As used herein, the term "characteristic parameter" means any property representative of the sample which is measured differentially with respect to the reference. Characteristic parameters include, but are not limited to, differential power input, differential heat flow, differential temperature, dielectric constant, and differential weight loss.

The reference 56 and sample 58 are subjected to a programmed heating or cooling program, in accord with a prescribed function, through a process of programmed and balanced heating. The programmed heating or cooling run subjects the sample and reference to an externally applied disturbance. The term "applied disturbance", as used herein, means a physical stress applied to both the sample and reference which permits, in accord with the differential technique used, the measurement of a characteristic parameter of the sample. In DSC and DTA, the applied disturbance is heat which induces a change in temperature (though not a change in average temperature if an isothermal function is used). In DDA, the applied disturbance is an electric field. In DPC, the applied disturbance is a lightwave.

Both the programmed heating and the balanced heating are performed through the reference heater 50 and the sample heater 48 in the reference and sample bases 52, 46. The heaters are powered with alternating current, and on one half-cycle the power supplied to both heaters is controlled by the temperature programmer 60. On the other half-cycle, however, a different power is supplied to each heater to nullify any temperature differential between the sample and the reference as sensed with the platinum resistance thermometers 54, 55 in the container bases. Thus, the heating system has two control loops, one responding to the temperature program and the other responding to the different energy requirements of the sample and reference. The average temperature amplifier 62, average temperature computer 64, recorder 68 and differential temperature amplifier 66 interact to maintain the two control loops as explained with respect to FIG. 1 in the following paragraph. The instrument responds very rapidly so that the deviation of the sample temperature from the reference temperature is negligible, and therefore the sample temperature follows the predetermined program even though it may undergo a thermal event (such as a phase or glass transition).

The system of FIG. 1 can be divided into two separate control loops, one loop for average temperature control and the other for differential temperature control. In the average temperature control loop, the programmer 60 provides a signal which is proportional to the desired temperature of the sample holder 58 and the reference holder 56. The programmer information is also relayed to the recorder 68 and appears as the abscissa scale marking. The programmer signal reaches the average temperature amplifier 62 and is compared with signals received from resistance thermometers 54, 44 via the average temperature computer 64. If the average temperature is greater than the temperature called for by the programmer 60, then the power supplied to the sample and reference heaters 48, 50 is decreased, and vice versa if the average temperature is less than that called for by the programmer 60.

In the differential temperature control loop, temperature signals received from the resistance thermometers 44, 54 are relayed to the differential temperature amplifier 66 via a comparator circuit (not shown) which determines whether the sample or reference temperature signal is greater. The differential temperature amplifier 66 responds to a disparity in the sample and reference temperature signals by adjusting the differential power increment fed to the sample and reference heaters 48, 50 to correct the temperature difference. A signal proportional to the differential power is sent to the recorder 68. The recorder 68 relays the differential signal to computing device 69 which processes the signal to provide the user with the characteristic parameter of the sample. Such computing devices include any appropriate commercially-available device, including desktop personal computers, such as the Perkin-Elmer Unix 7-Series data station.

Figure 2:
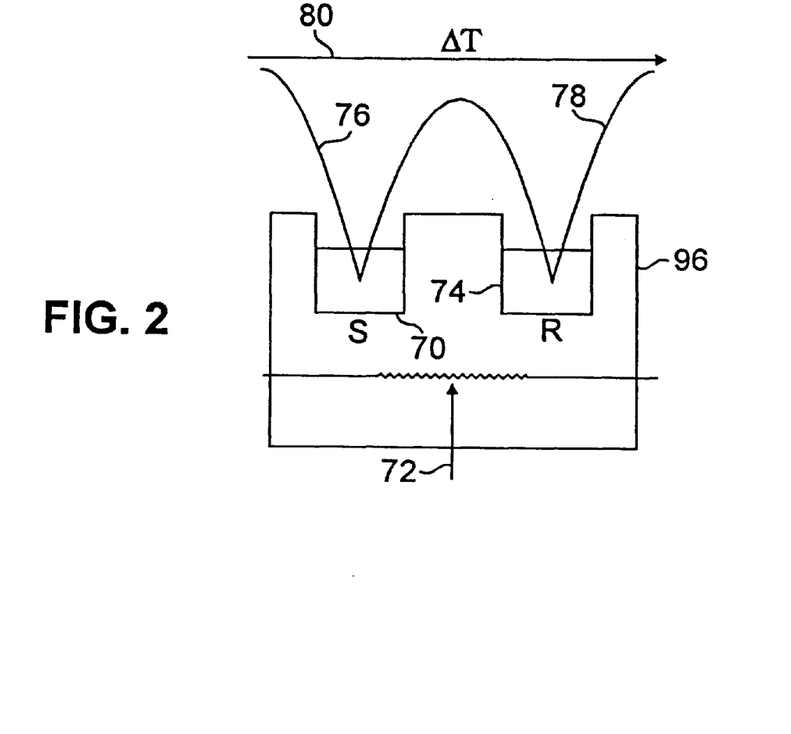
FIG. 2 is a schematic diagram illustrating a DTA instrument which is adapted to implement the present invention.
Figure 3:
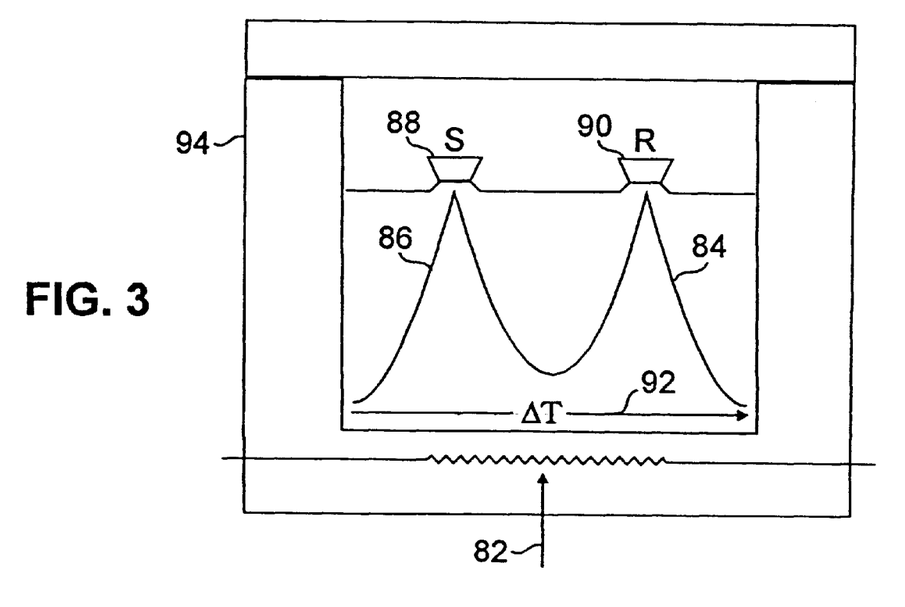
FIG. 3 is a schematic diagram illustrating a "heat flux" differential scanning calorimeter which is adapted to implement the present invention.

The foregoing description relating to FIG. 1 is directed to "power compensation" DSC. The structure of the apparatus for the present invention also includes instrumentation for "heat flux" DSC, as depicted in FIG. 3, and differential thermal analysis (DTA), as depicted in FIG. 2. Unlike "power compensation" DSC, the signal obtained in DTA or "heat flux" DSC is derived from the temperature difference between the sample and reference. The distinction between DTA and heat flux DSC is not substantial, and thus it is possible to calibrate a differential thermal analyzer for use as a heat flux DSC. Such a modification is described in F. Hongtu, P. G. Laye, Thermochim. Acta 153, 311 (1989).

In power compensation DSC, the sample and reference are provided with individual heaters. As shown in FIG. 2, the DTA technique provides an instrument 96 with a single heater 72 for both sample 70 and reference 74. Heat flux DSC, as shown in FIG. 3, provides an instrument 94 with a single heater 82 which heats both sample 88 and reference 90. In DTA, the temperatures of the sample and reference are detected, respectively, by sensors 76 and 80 which can be imbedded in the sample and reference materials. Heat flux DSC, on the other hand, uses a sample temperature sensor 86 and a reference temperature sensor 84, which are attached to a conductive membrane under pans which hold the sample and reference materials. In both DTA and heat flux DSC, the differential temperature 80 (FIG. 2) and 92 (FIG. 3) is determined. The DTA and heat flux DSC techniques, while considered to be inherently less quantitative than DSC, can be used to implement the method and apparatus of the present invention.

Theory—Introduction

Employing a conventional DSC, the sample and reference are heated or cooled at a constant rate $\beta_0$. The measurement signal represents the differential heat flow required to maintain the rate $\beta_0$.

In one embodiment of the present invention, a sinusoidal temperature oscillation is superimposed on the linear temperature change $\beta_0$, so that the temperature of sensing elements 44, 54 (FIG. 1) obeys eq. (1):

$$T(t)=T_0+\beta_0 t+T_a \sin \omega_0 t \qquad (1)$$

where $T_0$ is the initial temperature, $T_a$ is the amplitude of the sinusoidal temperature change, and $\omega_0$ is the cyclic frequency.

Theory Underlying The Prior Art

The method disclosed in the '775 patent proceeds from the assumption that the following is valid for the measured heat flow $\Phi$ (see for example eq. (1) in M. Reading et al., "Some Aspects of the Theory and Practice of Modulated Differential Scanning Calorimetry", Proceedings of the 1992 NATAS Conference, at page 145):

$$\phi(t) = \frac{dQ}{dt} = C_p \frac{dT}{dt} + f(t, T) \qquad (2)$$

where $C_p$ is the heat capacity of the sample, and f(t,T) describes the kinetic component of the DSC signal due to any physical or chemical transformation.

Interpreting eq. (2), if the heat capacity is determined by an independent method, then, according to the prior art, from a conventional DSC curve the kinetic component can be obtained using simple subtraction.

Phenomenologically, one can describe the measured heat flow as follows:

$$\Phi(T)=\Phi_D(T)+\Phi_a(T)\cos(\omega_0 t+\psi) \qquad (3)$$

where $\Phi_D$ is identical to the conventional DSC signal.

From the amplitude of the modulated component $\Phi_a$ the heat capacity is calculated thus:

$$C_p(T) = \frac{\Phi_a(T)}{T_a} \cdot \frac{1}{\omega_0} \qquad (4)$$

One then obtains the "rapidly reversible" component ($\Phi_{rev}$) of the measured signal as follows:

$$\Phi_{rev}(T)=C_p(T)\cdot\beta_0 \qquad (5)$$

The kinetic component ("non-rapidly reversible" heat transfer) is then $$\Phi_{non}(T)=\Phi_D(T)-\Phi_{rev}(T) \qquad (6)$$

These equations follow the method disclosed in the '775 patent.

Theory Underlying the Invention

Time-Dependent Linear Phenomena

If a physical system is in equilibrium, then no energy loss (dissipation) occurs, and the entropy remains unchanged (second law of thermodynamics). The system can then be described by time-independent potentials and the material properties are described by time-independent parameters (such as dielectric constant, compressibility modulus or heat capacity). In this case the DSC measurement curves are described, excluding the effects of thermal conduction, by equilibrium thermodynamics.

However, many thermal events are dependent on time and linked with energy loss (dissipation, or entropy change). Such events include biological processes, chemical reactions, glass transitions, and kinetically determined phase transitions. If the system is near equilibrium and if disturbances of the system during measurement are sufficiently small-scale, these events can be described by a linear response theory (see R. Kubo, Rep. Prog. Phys. 29, 255 (1966)).

If the measurement involves a disturbance by an intensive variable (such as temperature), then an extensive variable is measured (such as enthalpy H). In accord with the present invention, the relevant material property of the sample (such as heat capacity) can then be associated with an autocorrelation or retardation function $\phi(t)$.

Most generally, one can write a relationship between variations in temperature and the corresponding variations in enthalpy as follows:

$$\partial H(t) = \int_{-\infty}^{t} \phi(t-t')\partial T(t')dt' \qquad (7)$$

Eq. (7) provides an implicit definition of the autocorrelation function. One may then define a frequency-dependent complex heat capacity in the following manner:

$$C(\omega) = \int_{-\infty}^{\infty} \phi(t)e^{i\omega t}dt \tag{8}$$

with $$C(\omega)=C'(\omega)+iC''(\omega) \tag{9}$$

where i is the imaginary unit (i=√−1).

The real portion of the heat capacity C' describes energy storage, and in an equilibrium case matches $C_p$. As used herein, the terms "real" component (or portion) and "energy storage" component are interchangeable. The imaginary portion C" relates to the energy loss, and thus the terms "imaginary" component (or portion) and "energy loss" component are interchangeable.

In DSC measurements, heat flow $$\Phi = \frac{dH}{dt} \tag{10}$$

is the measurement variable.

By inserting eq. (10) into eq. (7), one obtains the following for the measurement signal:

$$\Phi(t) = \int_0^t \phi(t-t')\beta(t')dt' \tag{11}$$

with $$\beta(t) = \frac{dT}{dt} \tag{12}$$

For the case of linear systems, eq. (11) is the correct tool for describing a differential thermal instrument employing a prescribed function comprising a periodic part superimposed on a linear scan. This equation stands in contrast to eq. (2) of the prior art.

Heat Flow Under Isothermal Conditions

Isothermal conditions, as described here, mean that the temperature is altered according to a periodic function (a sinusoidal function in the following eqs.) with a sufficiently small amplitude $T_a$ about a constant temperature $T_0$:

$$T(t)=T_0+T_a \sin(\omega_0 t) \tag{13}$$

For the temperature change β, it follows that $$\beta(t)=\omega_0 T_a \cos(\omega_0 t) \tag{14}$$

Insertion of equation eq. (14) into eq. (11) yields $$\Phi(t) = \omega_0 T_a \int_0^t \phi(t-t')\cos(\omega_0 t')dt' \tag{15}$$

with the solution:

$$\Phi(t)=\omega_0 T_a[C'(\omega_0) \cos(\omega_0 t)+C''(\omega_0) \sin(\omega_0 t)] \tag{16}$$

or $$\Phi(t)=\omega_0 T_a |C(\omega_0)| \cos(\omega_0 t-\phi) \tag{17}$$

with $$|C|=\sqrt{C'^2+C''^2} \tag{18}$$

$$\tan\varphi = \frac{C''}{C'} \tag{19}$$

The solution represented by eq. (16) is the result of the following derivation (eqs. (A2)–(A5)). The fourier transformation of a convolution product (eq. 15) reduces to a simple algebraic product according to:

$$\mathcal{F}(\Phi(t)) = \Phi(\omega) = \frac{1}{2}\omega_0 T_a \phi(\omega)[\delta(\omega-\omega_0)+\delta(\omega+\omega_0)] \tag{A2}$$

where δ(ω) is the Dirac function.

The inverse transformation of eq. (A2) then yields the time-dependent heat flow:

$$\mathcal{F}^{-1}(\Phi(\omega)) = \Phi(t) = \frac{1}{2}\omega_0 T_a \int_0^\infty \phi(\omega)[\delta(\omega-\omega_0)+ \tag{A3}$$

$$\delta(\omega+\omega_0)]e^{i\omega t}d\omega$$

$$= \frac{1}{2}\omega_0 T_a[\phi(\omega_0)e^{i\omega_0 t}+\phi(-\omega_0)e^{i\omega_0 t}]$$

Since $\phi(\omega)=C^*(\omega)$ (see eq. (8)) and since $\phi(\omega)=\phi^*(-\omega)$ because φ(t) is real, it follows that:

$$\Phi(t)=\omega_0 T_a Re[C(\omega_0)e^{i\omega_0 t}] \tag{A4}$$

or $$\Phi(t)=\omega_0 T_a[C'(\omega_0) \cos(\omega_0 t)+C''(\omega_0) \sin(\omega_0 t)] \tag{A5}$$

If $\Phi_a$ is the heat flow amplitude (see eq. (17)), then one obtains the amplitude of the complex heat capacity from $$|C(\omega_0)| = \frac{\Phi_a(\omega_0)}{T_a \omega_0} \tag{20}$$

From this quantity, and the phase shift between heat flow and temperature, φ, the energy storage and energy loss components of heat capacity can be determined. In general the two components are functions of the measurement frequency.

A comparison of eq. (20) and eq. (4) shows that the two equations are identical only when C"(ω₀)=0 is valid. However, this is only realized if the heat capacity is not time-dependent (equilibrium). A correct interpretation of time-dependent processes in non-equilibrium thus appears not to be possible with prior art methods.

Heat Flow With a Linear Scan

If a sinusoidal oscillation function is superimposed on a linear heating rate $\beta_o$, the following can be written:

$$T(t)=T_0+\beta_0 t+T_a \sin(\omega_0 t) \tag{21}$$

$$\beta(t)=\beta_0+\omega_0 T_a \cos(\omega_0 t) \tag{22}$$

As eq. (3) shows, the measured heat transfer is composed of the superposition of a non-periodic function on a periodic one. So that the phase shift φ and the amplitude $\Phi_a$ may be determined with sufficiently small error, it is necessary that the non-periodic component be regarded as constant at least for one period of the periodic component. For this, it is required to have a thermal event that evolves sufficiently slowly and a low heating rate.

$\beta_o$ may be considered sufficiently small if:

$$\frac{\beta_0}{\omega_0} < 1 \tag{23}$$

Under this condition, one obtains through insertion of eq. (22) into (11):

$$\Phi(T) = C_\beta(T)\beta_0 + \omega_0 T_a |C(T,\omega_0)| \cos(\omega_0 t - \phi) \tag{24}$$

$C_\beta$ does not correspond to the equilibrium heat capacity $C_P$, but rather to that which is determined from a conventional DSC measurement with a linear heating rate of $\beta_o$.

If a pure relaxation transition is investigated, one obtains the overall information (the complex heat capacity) directly from the periodic component of the heat flow.

In order to compare the prior art method with the present invention, we consider the simplest model to describe the time dependence of a dynamic system, in which the retardation function corresponds to an exponential function, and neglect the effect of non-equilibrium. Then the following is valid for the complex heat capacity:

$$c^*(\omega) = \frac{C_p - C_\infty}{1 + i\omega\tau} + C_\infty \tag{25}$$

or $$c'(\omega) = \frac{C_p - C_\infty}{1 + \omega^2\tau^2} + C_\infty \tag{26}$$

and $$c''(\omega) = \frac{(C_p - C_\infty)\omega\tau}{1 + \omega^2\tau^2} \tag{27}$$

where $C_P$ is the heat capacity in equilibrium ($\omega \to 0$), $C_\infty$ the heat capacity for $\omega \to \infty$, and $\tau$ the relaxation time.

With a sinusoidal function superimposed on a linear heating scan, $C_P$ is replaced by $C_\beta$. From the amplitude of the periodic component one determines the amplitude of the complex heat capacity (see eq. (20)). To obtain the "non-rapidly reversible" heat flow $\Phi_{non}$, in accord with the prior art method, $|C|$ is subtracted from $C_\beta$ (see eqs. (6) and (24)). By insertion of eq. (25) into eq. (24), it is possible to verify that the following is valid:

$$\Phi_{non}(T,\omega_0) = [C_\beta(T,\omega_\beta) - |C(T,\omega_0)|]\beta_0 \approx (C_\beta(T,\omega_\beta) - \sqrt{C'(T,\omega_0)C_{P(T)}})\beta_0 \tag{28}$$

For the "rapidly reversible" heat flow one obtains:

$$\Phi_{rev}(T,\omega_0) = |C(T,\omega_0)|\beta_0 \approx \sqrt{C_P(T)C'(T,\omega_0)}\beta_0 \tag{29}$$

The derivation of eqs. (28) and (29) follows from eqs. (A6)–(A10) as described below. By elimination of $\omega\tau$ from eqs. (26) and (27) one obtains the equation (Cole-Cole-Bergen):

$$\left(C' - \frac{C_p + C_\infty}{2}\right)^2 + C''^2 = \left(\frac{C_p - C_\infty}{2}\right)^2 \tag{A6}$$

Following elementary transformations one obtains:

$$|C|^2 = C'^2 + C''^2 = C'(C_P + C_\infty) - C_P C_\infty \tag{A7}$$

Assuming that:

$$C_P C_\infty \cong C'C_P \tag{A8}$$

it follows that:

$$|C|^2 = C'C_P \tag{A9}$$

from which eq. (29) follows for the "rapidly reversible" heat flow.

For the "non-rapidly reversible" heat flow, $$C_\beta - |C| \cong C_\beta - \sqrt{C'C_P} \tag{A10}$$

from which eq. (28) follows.

Only $C_\beta$ and $C'$ contribute to the development of a peak in $\Phi_{non}$. With the prior art method there can never be a separation of the energy loss processes since $C''(\omega_0)$ is not contained in eq. (28). $\Phi_{non}$ is merely the difference between two measurements obtained under dissimilar experimental conditions and is not amenable to physical interpretation.

From eqs. (20), (28) and (29) it is evident that the prior art method provides results that can be correctly interpreted only under equilibrium conditions. Since, in such a case, $C' = C_P$ and $C'' =$ ), it follows that $$\Phi_{rev} = C_P \beta_o \tag{30}$$

and $$\Phi_{non} = 0 \tag{31}$$

In assessing glass transitions, more significant information is gained if determinations are made of the energy storage component of heat flow:

$$\Phi_{stor}(T,\omega_0) = C'(T,\omega_0)\beta_0 = |C(T,\omega_0)|\beta_0 \cos\phi \tag{32}$$

and the energy loss component of heat flow $$\Phi_{loss}(T,\omega_0) = C''(T,\omega_0)\beta_0 = |C(T,\omega_0)|\beta_0 \sin\phi \tag{33}$$

Only the energy storage and energy loss components of the heat flow have thermodynamic and physical significance for both time-dependent and time-independent thermal events.

If a time-dependent reaction occurs, then on neglecting the entropy variation, we find:

$$f_T(t) = \left(\frac{dQ}{dt}\right)'_{P,T} = -mq_{P,T}v \tag{34}$$

where $mq_{P,T}$ is the heat of reaction $v$ is the rate of reaction $f_x(t)$ is the heat flow measured under isothermal conditions.

To find the heat flow during a temperature scan, it is necessary to know the temperature dependence of f ($\alpha_f = df/dT$). Using a linear approximation and the principle of superposition, we find for the relevant part of the heat flux:

$$\Phi_r(T) = f_{T=T_0}(t) + \int_0^t \alpha_f(t - t')\beta(t')dt' \tag{35}$$

If the measurement is started at a sufficiently low temperature, the first term on the right hand side of eq. (35) may be neglected. A comparison of eqs. (11) and (35) indicates that the principle underlying data reduction in the present case will be identical to that explained previously. However, the interpretation of the results will be different.

If the sample is sufficiently far removed from its actual equilibrium state, then the linear approximation is no longer valid. In this case, $\Phi_r$ contains no information on such reactions, which, therefore, can be detected only in the conventional DSC signal (or the averaged heat flow $\Phi_D$). C'(T)$\beta_o$ may then be used as a baseline for the analysis of the DSC signal measured in such reactions.

Effect Of Thermal Conduction On The Measurement Signal

The temperature sensor of a DSC is not directly in contact with the sample. Between the sample and the sensor, and within the sample itself, there is some thermal resistance to heat flow. Therefore, there is a difference between the measured temperature T and the sample temperature $T_s$. For the case of an isothermal, sinusoidally oscillated scan, the following is valid for the sample temperature:

$$T_s(t)=T_0+T_a \sin \omega_0 t \tag{36}$$

The corresponding temperature change is $$\beta_s(t)=\omega_0 T_a \cos \omega_0 t \tag{37}$$

The effect of the thermal resistance on the measurement signal may be assessed as follows:

$$T(t) = \int_0^t G(t-t')T_a(t')dt' \tag{38}$$

and $$\beta(t) = \int_0^t G(t-t')\beta_s(t')dt' \tag{39}$$

G(t) is the function through which the thermal resistance is described. G(t) is real.

By solving equation (39) and inserting its solution into equation (11), one obtains the following for the measured heat flow:

$$\Phi(t)=\omega_0 T_a |G(T,\omega_0)| \, |C(T,\omega_0)| \cos (\omega_0 t-\phi-\phi_g) \tag{40}$$

The solution follows from eqs. (A11)–(A17).

Insertion of eq. (37) into eq. (39) and the subsequent Fourier transformation of the convolution product yields, similarly to eq. (A2):

$$\beta(\omega) = \frac{1}{2}\omega_0 T_a G(\omega)[\delta(\omega-\omega_0)+\delta(\omega+\omega_0)] \tag{A11}$$

By Fourier transformation of eq. (11), $$\Phi(\omega)=\Phi(\omega)\beta(\omega) \tag{A12}$$

Using eq. (A11), $$\Phi(\omega) = \frac{1}{2}\omega_0 T_a C^*(\omega)G(\omega)[\delta(\omega-\omega_0)+\delta(\omega+\omega_0)] \tag{A13}$$

The inverse transformation yields $$\Phi(t) = \frac{1}{2}\omega_0 T_a [C^*(\omega_0)G(\omega_0)e^{i\omega_0 t}+C^*(-\omega_0)G(-\omega_0)e^{i\omega_0 t}] \tag{A14}$$

Since G(t) is real, $G(\omega)=G^*(-\omega)$. Hence, $$\Phi(t)=\omega_0 T_a Re[C^*(\omega_0)G(\omega_0)e^{i\omega_0 t}] \tag{A15}$$

or $$\Phi(t)=\omega_0 T_a Re[|c(\omega_0)||G(\omega_0)|e^{i(\omega_0 t-\phi+\phi_g)}] \tag{A16}$$

$$=\omega_0 T_a|G||C|\cos(\omega_0 t-\phi+\phi_g) \tag{A17}$$

It can be recognized that the amplitude of the heat flow is modified by |G|, and that owing to the thermal resistance, an additonal phase shift $\phi_g$ comes into existence.

This influence of thermal conduction can be eliminated by means of a calibration. For this, a substance is needed with no energy loss component in its heat capacity, such as sapphire.

The calibration factor for the amplitude is obtained from $$K = \frac{\omega_0 T_a C_p(T_a)}{\Phi_a(T_a, \omega_0)} \tag{41}$$

When using the sapphire standard, the phase shift between temperature and heat flow is $\phi_g$.

It can be shown that the calibration factor K is of the form $$K=K(\omega_0, k_s, T_a, T) \tag{42}$$

where $k_s$ is the heat transfer coefficient between the sample and the temperature sensor. In the case of sufficiently thin samples, it can be shown that the above function (42), in fact, reduces to K'($\omega_0$, $\phi$) where $\phi$ is the heat flow phase, measured in the absence of any time-dependent thermal event. The calibration factor K, or K'(107 $_0,\phi$), represents a universal calibration function which incorporates implicitly physical properties of the sample (e.g., heat transfer) through its dependence on $\phi$. This function can be determined for any instrument (whether a DTA or a DSC of the heat flux or power compensation type) using a known standard, such as sapphire. Once obtained it can be used in a wide range of temperatures, scanning rates or oscillation periods and allows the user to measure absolute (as opposed to relative) values of the complex specific heat for any sample.

Implementation of an Embodiment of the Invention

The following is a step-by-step description of an embodiment of the method and apparatus of the invention. Other embodiments will be apparent to those skilled in the art.

The user selects a linear temperature program that consists of any number of heating or cooling scans, each of which is preceded and followed by an isothermal segment. The user also selects an oscillation period and an oscillation amplitude.

The instrument 10 (FIG. 1) records the sample temperature, as measured by the sensor 44 located close to the sample material, and, for a power consumption DSC, the differential power that is applied to maintain the sample and the reference at the same temperature throughout the applied temperature program. For a heat flux DSC, the instrument 94 (FIG. 3) records the sample temperature as measured by a sensor 86 located close to the sample material and the differential heat flow. In a DTA instrument 96 (FIG. 2), a sensor 76 imbedded in the sample material measures the sample temperature and the differential heat flow. The recorded signals are analyzed over a moving interval in order to retrieve the analytically significant information.

The analysis proceeds in accord with the following steps:

1. Extract the conventional DSC signal and temperature: At each point, the normalized numerical integral of the heat flow and temperature, over an interval consisting of exactly an integer number of oscillation periods and centered on that point, is calculated. The results represent the average heat flow and average temperature associated with the centroid of the integration interval. These quantities will be referred to as the DC signals ($\phi_{DC}$ and $T_{DC}$).

2. Extract the pure oscillated heat flow and temperature signals: On a point by point basis, the DC signals ($\phi_{DC}$ and $T_{DC}$) are subtracted from the recorded signals. This operation yields the pure oscillated signals, which will be referred to henceforth as the AC signals ($\phi_{AC}$ and $T_{AC}$).

3. Calculate the in-phase and in-quadrature components of the AC signals: At each point, the numerical integral of the AC signals ($\phi_{AC}$ and $T_{AC}$) suitably multiplied by sine and cosine functions, over an interval consisting of exactly an integer number of oscillation periods and centered on that point, is calculated. Using the orthogonality property of circular functions over an integer number of periods, the inphase ($\phi_{sin}$ and $T_{sin}$) and quadrature ($\phi_{cos}$ and $T_{cos}$) components of the AC signals can be derived from the integration results. Each component is associated with the centroid of the integration interval.

Figure 12:
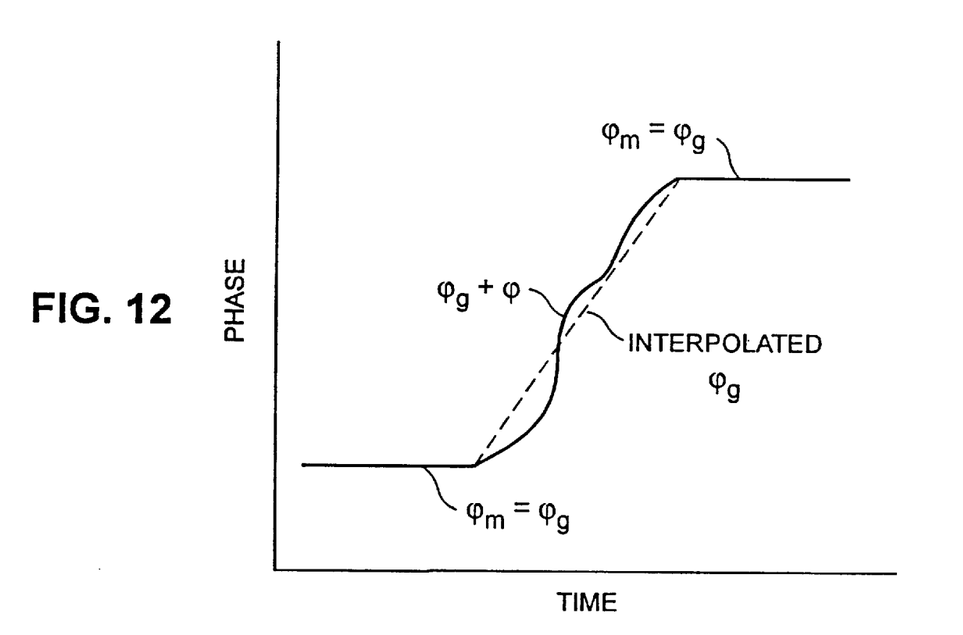
FIG. 12 is a graph representing an interpolation method for determining $\psi_g$.

4. Calculate the actual heat flow phase $\phi_g$: At each point of an underlying isotherm, the difference between the measured heat flow phase ($\phi_m = \tan^{-1}(\phi_{sin}/\phi_{cos})$) and the temperature phase ($\phi_T = -\tan^{-1}(\phi_{cos}/\phi_{sin})$) is obtained ($\phi_g = \phi_m - \phi_T$). The value of $\phi_g$ during the scanning portion of the underlying linear temperature program is then calculated by linear interpolation between the values derived in the adjoining isothermal portions of the underlying linear temperature program. The method of interpolation is illustrated by FIG. 12.

5. Calculate the instantaneous calibration constant: At each point, the actual heat flow phase $\phi_g$, as calculated in the previous step, is used as an argument in a universal calibration function to obtain the specific heat calibration constant K appropriate to the actual experimental conditions extant for that particular point.

6. Calculate the real and imaginary components of the specific heat: C' and C" are calculated at each point by solving the following set of simultaneous equations:

$C'\cos(\phi_g+\phi_T)-C''\sin(\omega_g+\phi_T)=K\phi_{cos}/(T_a\omega)$ $C'\sin(\phi_g+\phi_T)-C''\cos(\omega_g+\phi_T)=K\phi_{sin}/(T_a\omega)$ where $T_a=(T_{cos}^2+T_{sin}^2)^{1/2}$ and $\omega$ is the circular frequency corresponding to the applied oscillation's period. The value K in the above equations for calculation of the real component of the specific heat (C') and the imaginary component of the specific heat (C") is the instantaneous calibration constant calculated in step 5, above.

7. Smooth the calculated signals: $\phi_{DC}$, C' and C" are smoothed at each point by normalized numerical integration over an interval consisting of exactly an integer number of oscillation periods and centered on that point. Each calculated value is associated with the centroid of the integration interval.

EXAMPLES

The following experimental data were obtained using a Perkin-Elmer DSC-7 "power compensation" Differential Scanning Calorimeter connected to a Perkin-Elmer TAC-7/DX Thermal Analysis Controller that communicates with a Perkin-Elmer Unix 7-Series data station. All samples used in the experiments are readily available commercial products. Sample sizes are as indicated below.

FIG. 4

Figure 4:
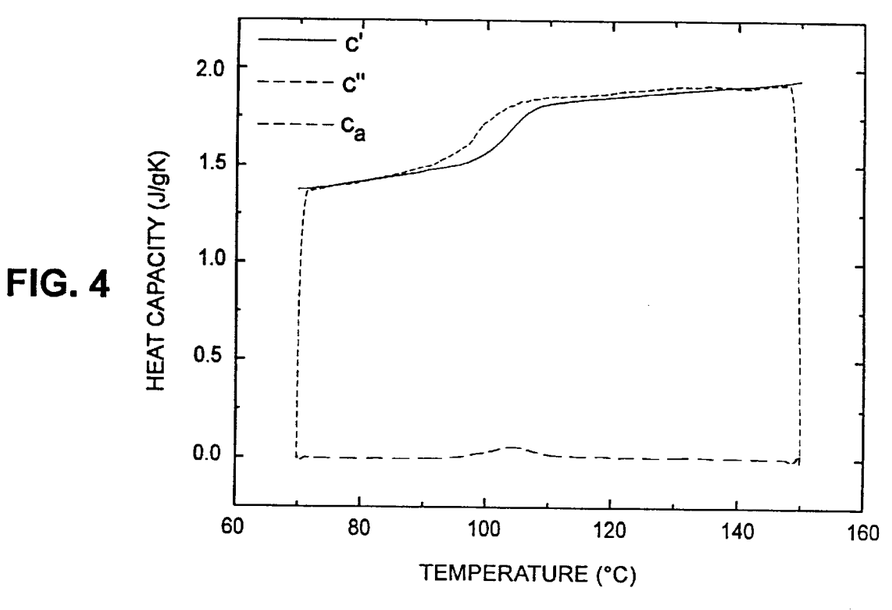
FIG. 4 is a plot of heat capacity vs. temperature with data representing average heat capacity, the energy storage (real) portion of the heat capacity and the energy loss (imaginary) portion of the heat capacity which are obtained according to the method and apparatus of the present invention.

FIG. 4 shows the glass transition of polystyrene (PS), measured in a cooling run, ($\beta_0=-1$ K/min, Oscillation amplitude $T_a$–1 K, Period=100 sec, Sample weight=17.452 mg).

The heat capacity $C_a$ is calculated from the average heat flow $\phi_D$. $C_a$ is equal to the value obtained with a conventional DSC and is identical to $C_\beta$. The inflection point in $C_a$ occurs at a lower temperature than that of C'. In contrast to C', the $T_g$ measured using $C_a$ depends on $\beta_0$. The inflection point of the real (energy storage) part, C', is correlated with the peak in the imaginary (energy loss) part, C". Both the shape and the temperature dependence of C' and C" are in accord with the theories of relaxation in glass transition.

FIG. 5

Figure 5:
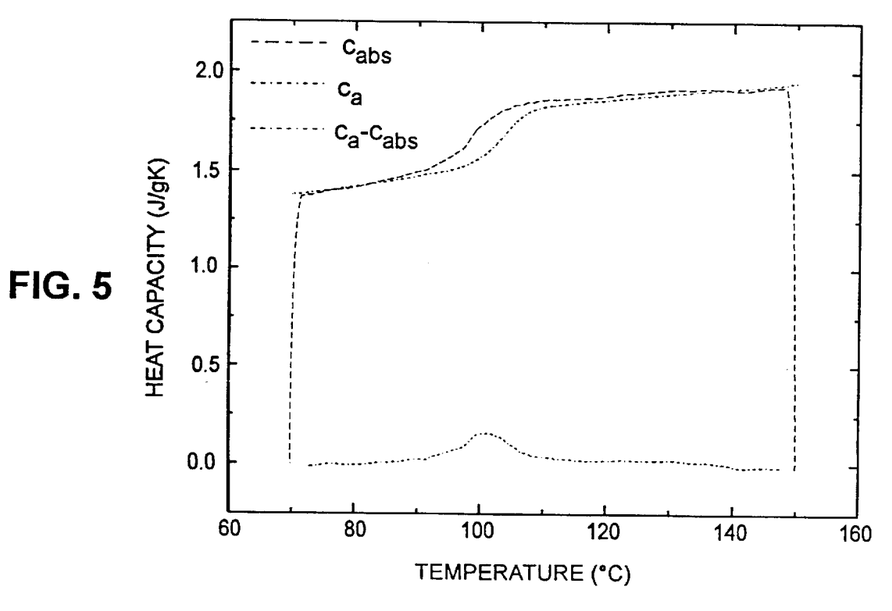
FIG. 5 is a plot of heat capacity vs. temperature with data representing average heat capacity, the absolute value of the heat capacity and the difference between the average and absolute heat capacity.

The heat capacities $C_{abs}$ (absolute heat capacity) and $C_a$ (average heat capacity), and their difference $C_a - C_{abs}$, are shown for the same measurement as in FIG. 4.

FIG. 5 depicts the prior art calculation (from the '775 patent). $C_a - C_{abs}$ indeed exhibits a peak; however, it is located at lower temperature than the glass transition (as calculated from C') and is dependent on the cooling rate $\beta_0$. As explained with regard to eq. (28), this calculated value is non-quantitative regarding the relaxation process.

FIG. 6

Figure 6:
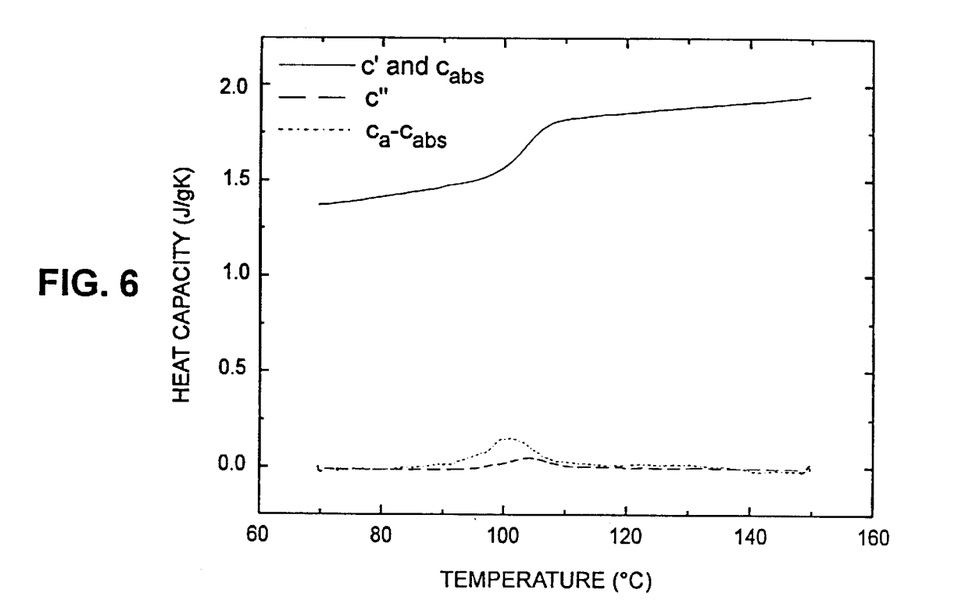
FIG. 6 is a plot of heat capacity vs. temperature with data representing the energy loss (imaginary) and energy storage (real) portions of the heat capacity, the absolute value of the heat capacity and the difference between the average and absolute heat capacity which are obtained according to the method and apparatus of the present invention.

The difference between the prior art ('775 patent) and the present invention is shown for the measurement of FIG. 4. As is apparent, C" and $C_a - C_{abs}$ exhibit a markedly different dependence on the temperature, with only the former having its peak correctly at the inflection point (glass transition temperature $T_g$) of the real part and absolute value of the complex specific heat.

FIG. 7

Figure 7:
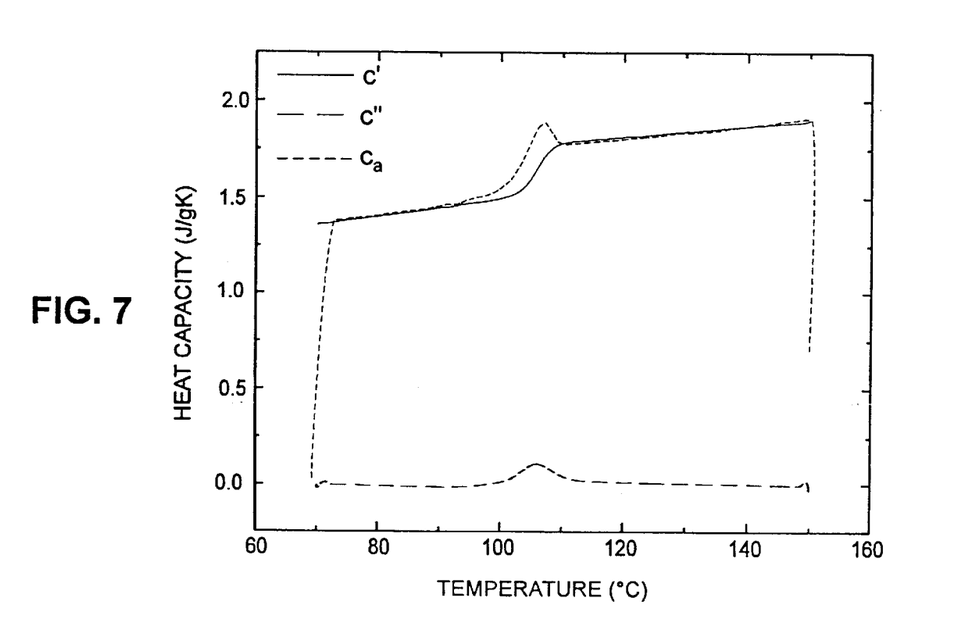
FIG. 7 is a plot of heat capacity vs. temperature with data representing the energy loss (imaginary) and energy storage (real) portions of the heat capacity, and the average heat capacity which are obtained according to the method and apparatus of the present invention.

Glass Transition of Polystyrene (PS), measured in a heating run ($\beta_0=2$ K/min, Oscillation amplitude $T_a=1$ K, Period=50 sec, Sample Weight=17.452 mg). The sample is identical to that used for the run of FIG. 4.

$C_a$ exhibits the same behavior as seen with a conventional DSC. An enthalphy relaxation peak is superimposed on the glass transition. C' has an inflection point similar to that of FIG. 4.

FIG. 8

Figure 8:
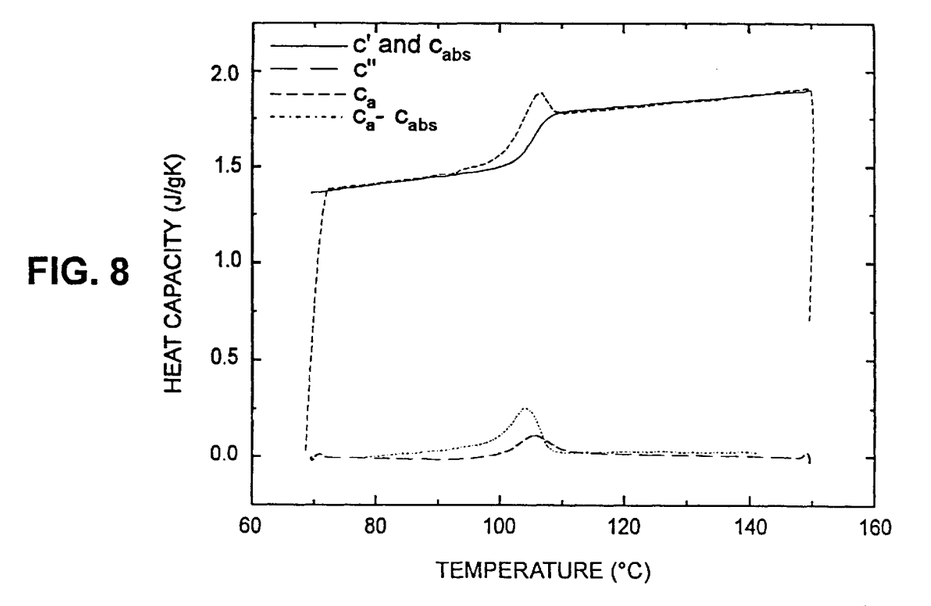
FIG. 8 is a plot of heat capacity vs. temperature with data representing the energy loss (imaginary) and energy storage (real) portions of the heat capacity, the absolute and average values of the heat capacity and the difference between the average and absolute heat capacity.

Calculation following the prior art ('775 patent). The interpretation of $C_a - C_{abs}$ suffers from the same difficulties as in FIG. 5: only C" has its peak correctly at the inflection point (glass transition temperature $T_g$) of the real part and absolute value of the complex specific heat.

FIG. 9

Figure 9:
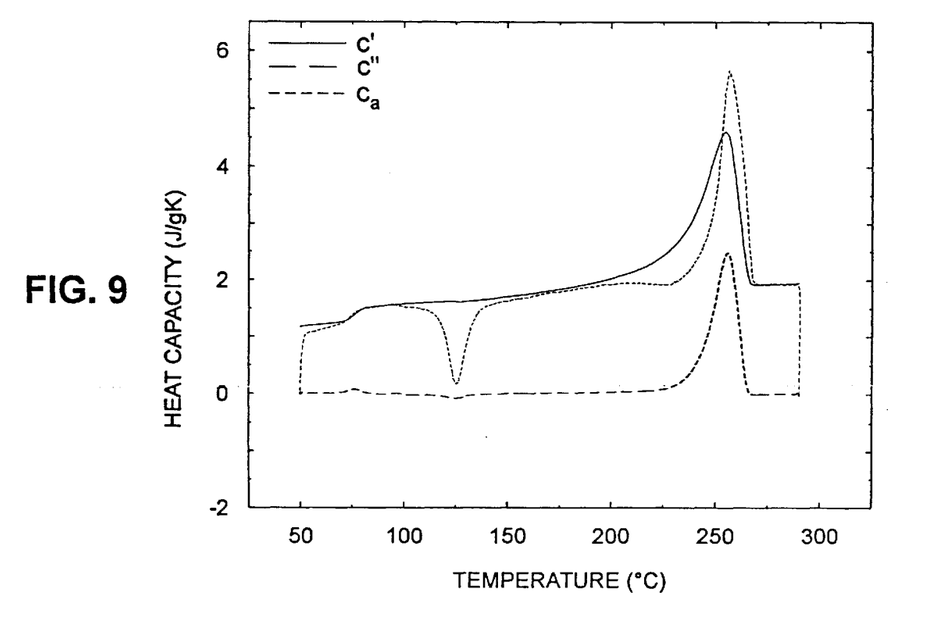
FIG. 9 is a plot of heat capacity vs. temperature with data representing the energy loss (imaginary) and energy storage (real) portions of the heat capacity, and the average heat capacity which are obtained according to the method and apparatus of the present invention.

Heating curve for quench cooled PET ($\beta_0=2$ K/min, Oscillation amplitude $T_a=1$ K, Period=60 sec, Sample Weight=5,842 mg).

Three transitions can be seen: the glass transitional around 70° C., the recrystallization around 120° C. and the melting around 200° C. The glass transition exhibits the same behavior as discussed for polystyrene. The recrystallization is a transition of the strongly undercooled melt in the polymer crystal. The melt is far removed from equilibrium. The transition is possible in only one direction and is therefore only barely seen in the modulated signal. Only C" has a small peak. C' can be used as a baseline in the evaluation of $C_a$. As far as the melting is concerned, C' exhibits a change at lower temperatures, while C" remains unchanged in that range. The peak maximum of C" occurs at a somewhat larger temperature than that of C'. Using irreversible thermodynmics, these curves give information on enthalpy changes and entropy.

FIG. 10

Figure 10:
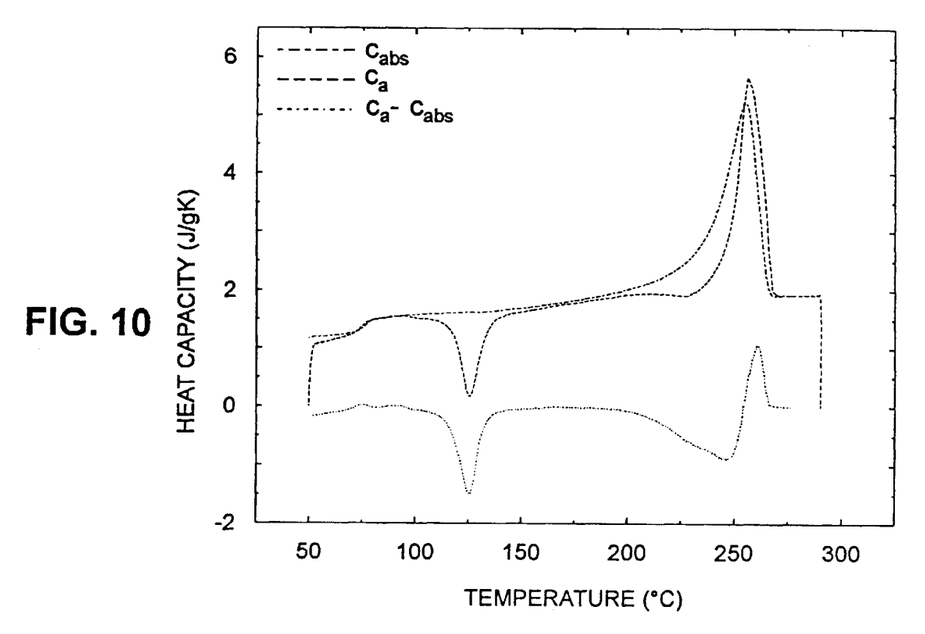
FIG. 10 is a plot of heat capacity vs. temperature with data representing the absolute and average values of the heat capacity and the difference between the average and absolute heat capacity.

Calculation following the prior art ('775 patent). $C_a-C_{abs}$ is really the difference between two curves obtained under dissimilar experimental conditions. It can be interpreted only intuitively, and not quantitatively.

FIG. 11

Figure 11:
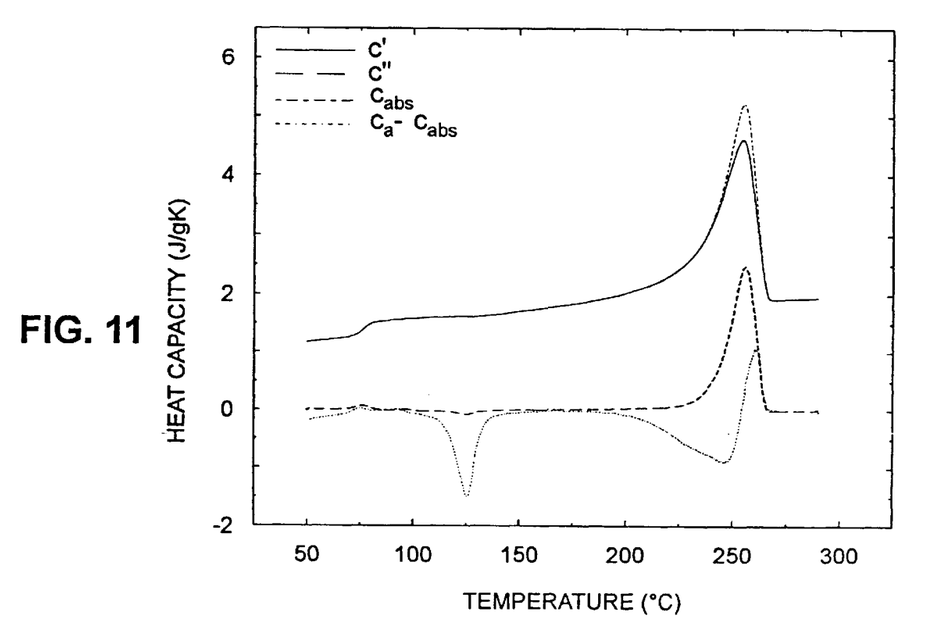
FIG. 11 is a plot of heat capacity vs. temperature with data representing the energy loss (imaginary) and energy storage (real) portions of the heat capacity, the absolute and average values of the heat capacity and the difference between the average and absolute heat capacity.

The difference between the prior art ('775 patent) and the present invention is shown for the measurement of FIG. 9: since, as explained with regard to FIG. 9, the recrystallization cannot affect the modulated signal, it is essentially not seen in either C' or C", while strongly present in $C_a$. In contrast, $C_a-C_{abs}$, the prior art "non-rapidly reversible" component, erroneously exhibits a strong peak at the recrystallization temperature. In addition, the latter quantity also evinces apparently unexplainable behavior around the phase transition temperature.

We claim:

1. A method of analyzing a sample using a differential analysis apparatus comprising:

determining a universal calibration function for the differential analysis apparatus, said calibration function defining a calibration constant in dependence on an attribute of the sample;

subjecting the sample and a reference to an externally applied disturbance in accord with a prescribed function comprising a periodically changing part having a specified frequency;

detecting a differential signal representative of at least one characteristic parameter of the sample;

processing said signal to determine the attribute of the sample, wherein said processing step utilizes data collected during the analysis of the sample and does not include the use of a separate calibration means during analysis of the sample;

using said attribute in said calibration function to determine the calibration constant, the calibration function being independent of the composition of the sample to be analyzed and the externally applied disturbance; and using the calibration constant to provide separate components relating to the at least one characteristic parameter of the sample.

2. The method of claim 1 wherein said separate components relate to an energy loss portion and an energy storage portion of said characteristic parameter.

3. The method of claim 2 wherein said applied disturbance is temperature change.

4. The method of claim 3 wherein said characteristic parameter is heat capacity.

5. The method of claim 3 wherein the prescribed function comprises a sinusoidal periodic function superimposed on a linear heating or cooling scan.

6. The method of claim 5 wherein a positive value of the linear rate of heating or cooling and a frequency of sinusoidal periodic function satisfy $$\frac{\beta_0}{\omega_0} < 1$$

wherein $\omega_0$ is the linear rate of heating or cooling and $\omega_0$ is the frequency of the sinusoidal periodic function.

7. The method of claim 3 wherein the characteristic parameter relates to a time-dependent thermal event of the sample.

8. The method of claim 1 wherein the attribute depends at least in part on a heat flow phase of the sample.

* * * * *